(12) United States Patent
Clymer et al.

(10) Patent No.: US 6,242,907 B1
(45) Date of Patent: Jun. 5, 2001

(54) APPARATUS AND METHOD OF DETERMINING THE ORIENTATION OF AN OBJECT RELATIVE TO A MAGNETIC FIELD

(75) Inventors: Mark L. Clymer, Mystic; Glenn Graves, Oakdale, both of CT (US)

(73) Assignee: Graves Electronics LLC, Oakdale, CT (US)

( * ) Notice: Subject to any disclaimer, the term of this patent is extended or adjusted under 35 U.S.C. 154(b) by 0 days.

(21) Appl. No.: 09/256,563

(22) Filed: Feb. 24, 1999

(51) Int. Cl.[7] ........................................ G01B 7/14
(52) U.S. Cl. .................. 324/207.17; 342/462; 342/463
(58) Field of Search .................... 324/207.23, 207.17; 702/150, 151, 152, 153; 342/462, 463

(56) References Cited

U.S. PATENT DOCUMENTS

| | | | |
|---|---|---|---|
| 5,525,901 | * | 6/1996 | Clymer et al. ............... 324/207.21 |
| 5,558,091 | * | 9/1996 | Acker et al. .................. 600/424 |
| 5,600,330 | * | 2/1997 | Blood .............................. 342/463 |
| 5,953,683 | * | 9/1999 | Hansen et al. ................... 702/95 |

* cited by examiner

*Primary Examiner*—Christine Oda
*Assistant Examiner*—Subhash Zaveri
(74) *Attorney, Agent, or Firm*—McCormick, Paulding & Huber LLP

(57) ABSTRACT

A method and apparatus for determining the orientation of an object relative to a reference magnetic field includes establishing generally adjacent to the object a modifiable magnetic field. The direction of the modifiable magnetic field is changed among a plurality of predetermined, known orientations relative to the object. A resultant magnetic field, including the reference magnetic field and the modifiable magnetic field, is repeatedly measured adjacent to the object. The step of measuring is directed outwardly from adjacent to the object in predetermined directions that are fixed relative to the object to determine when the magnitude of the resultant magnetic field is minimized or maximized indicating that the direction of the modifiable magnetic field is parallel with that of the reference magnetic field. Thereupon, the orientation of the object is correlated to the known orientation of the modifiable magnetic field.

22 Claims, 3 Drawing Sheets

APPARATUS AND METHOD OF DETERMINING THE ORIENTATION OF AN OBJECT RELATIVE TO A MAGNETIC FIELD

FIELD OF THE INVENTION

The present invention relates generally to an apparatus and method of determining the orientation of an object and more particularly to an apparatus and method of determining the orientation of an object relative to a magnetic field.

BACKGROUND OF THE INVENTION

Common practice at present for the measurement of angular orientation in three-dimensional space is to use three-axis magnetometers to resolve orientation of an object in a magnetic field such as, for example, the magnetic field of the Earth. The measurement of angular orientation may be employed, for example, in ambulatory systems, electronic guidance and compass systems. Ambulatory systems measure three-dimensional body segment motion such as, for example, fluctuations of movements in persons with degenerative neurological disorders, measuring the level of functional impairment in persons with rheumatic and musculoskeletal diseases, assessing gait and balance deficits in the elderly and persons with neurologic disease, monitoring and documenting the progression of neurological, rheumatic and musculoskeletal diseases and disorders, developing objective outcome measures of the efficacy of rehabilitation programs, surgical interventions, and drug treatments in human diseases and disorders that affect body movement, better understanding the injury mechanisms associated with occupational, recreational and sports activities, and assessing the performance of activities of daily living, as well as occupational, recreational and sports activities in the environments in which they are typically conducted.

A variety of sensors are known in the art for measuring magnetic fields such as, for example, Hall effect sensors, proton quantum interference detectors "SQUID", fluxgate magnetometers, inductive pickup sensors and magnetoresistive sensors.

Three-axis magnetometers that can be used to estimate orientation with respect to an ambient magnetic field, such as the Earth's magnetic field, are commercially available from several companies. However, the practical use of these systems has been restricted by several significant technical limitations. First, the accuracy of these devices is dependent on the sensitivity and offset of each sensor. Since these devices attempt to directly measure the magnetic field with the magnetic sensors themselves, each sensor must maintain zero and offset values, and have low drift characteristics with temperature change. Also, most magnetic field sensors measure sums of vector components of the imposed magnetic field, which makes the determination of orientation problematic unless precise knowledge of the local magnetic field is available. When employing the Earth's magnetic field, the system software that resolves the angular orientation from the sensor data must have accurate values for the magnitude and direction of the Earth's field vector for every location where the system is used. Databases are available that provide this information for specific locations (latitude and longitude) on the Earth's surface. However, there is no easy way to determine if the Earth's magnetic field is distorted in a particular area, and significant errors will result if the database information is used in such an area.

If the Earth's magnetic field is distorted, if the magnitude and direction of the Earth's magnetic field are unknown, or if the sensor offsets are changed, then the magnetometer must be recalibrated to maintain the accuracy of the measurements. The user can recalibrate by carefully rotating the magnetometer a full revolution about each of its three axes, while monitoring the output of the sensors. The validity of this calibration procedure is predicated on the three sensors having the same sensitivity.

Because of this burden of complexity, as well as the high price for such systems, the three orthogonal sensor system, or three-axis magnetometer, has not seen much practical use except in a tightly controlled laboratory environment. Thus, there is a need in the sensor art for a sensor system that may measure angular positioning in three axes while eliminating the burden of complexity that influences the operation of existing sensor art.

Accordingly, it is an object of the present invention to provide a sensor system which overcomes the above-described disadvantages of prior devices for determining the orientation of an object in a magnetic field.

The above and other objects and advantages of this invention will become more readily apparent when the following description is read in conjunction with the accompanying drawings.

SUMMARY OF THE INVENTION

According to a first aspect of the present invention, a method of determining the orientation of an object relative to a reference magnetic field includes the steps of establishing generally adjacent to the object a modifiable magnetic field. The direction of the modifiable magnetic field is repeatedly changed among a plurality of predetermined, known orientations relative to the object. A resultant magnetic field, including the reference magnetic field and the modifiable magnetic field, is measured adjacent to the object. The step of measuring is directed outwardly from adjacent to the object in predetermined directions that are fixed relative to the object. The method further includes determining when the magnitude of the resultant magnetic field is minimized or maximized indicating that the direction of the modifiable magnetic field is parallel with that of the reference magnetic field. Thereupon, the orientation of the object is correlated to the known orientation of the modifiable magnetic field.

According to a second aspect of the present invention, an apparatus for determining the orientation of an object relative to a reference magnetic field includes first means for establishing generally adjacent to the object a modifiable magnetic field. Second means is provided for changing the direction of the modifiable magnetic field among a plurality of predetermined, known orientations relative to the object. Third means repeatedly measures adjacent to the object a resultant magnetic field, including the reference magnetic field and the modifiable magnetic field, wherein the measuring is directed outwardly from adjacent to the object in predetermined directions that are fixed relative to the object. Fourth means determines when the magnitude of the resultant magnetic field is minimized or maximized indicating that the direction of the modifiable magnetic field is parallel with that of the reference magnetic field, and thereupon correlating the orientation of the object to the known orientation of the modifiable magnetic field.

According to a third aspect of the present invention an apparatus for determining the orientation of an object relative to a reference magnetic field includes a Helmholtz coil system having windings extending in three coordinate axes for generating a modifiable magnetic field when electrical current is passed through the windings. Each of the axes is generally orthogonal relative to each other. A controller directs current to the Helmholtz coil system and repeatedly changes the polarity and magnitude of the electrical current through each of the windings among a plurality of predetermined, known orientations relative to the object, and determines when a resultant magnetic field, including the reference magnetic field and the modifiable magnetic field, is minimized or maximized indicating that the reference magnetic field is parallel to the known orientation of the modifiable magnetic field. At least one magnetic sensor communicates with the controller. The at least one magnetic sensor is to be located adjacent to and in fixed orientation relative to the object for detecting the resultant magnetic field.

DETAILED DESCRIPTION OF THE PREFERRED EMBODIMENT

With reference to FIGS. 1–5, a scanning magnetic angle comparator system "SMAC" or sensor system embodying the present invention is generally designated by the reference number 10. The sensor system 10 detects the orientation or angular position in three axes of any three-dimensional object relative to an ambient or reference magnetic field, such as the Earth's magnetic field, by creating a modifiable magnetic field that is repeatedly changed in direction in small angle increments according to a predetermined pattern until the modifiable magnetic field minimizes, cancels or maximizes the reference magnetic field. At the moment of minimization or maximization, the modifiable magnetic field is parallel with the ambient or reference magnetic field, whereby the orientation or magnetic angle of the object relative to the reference magnetic field is indirectly determined by determining the orientation of the object relative to the known orientation of the modifiable magnetic field. The sensor system 10 is beneficial and will be described with respect to the development of ambulatory systems to measure three-dimensional human body movement in a real environment outside of the laboratory. It will be understood, however, that the sensor system 10 may be used in other applications where orientation of an object is critical such as electronic guidance and compass applications.

Figure 1:
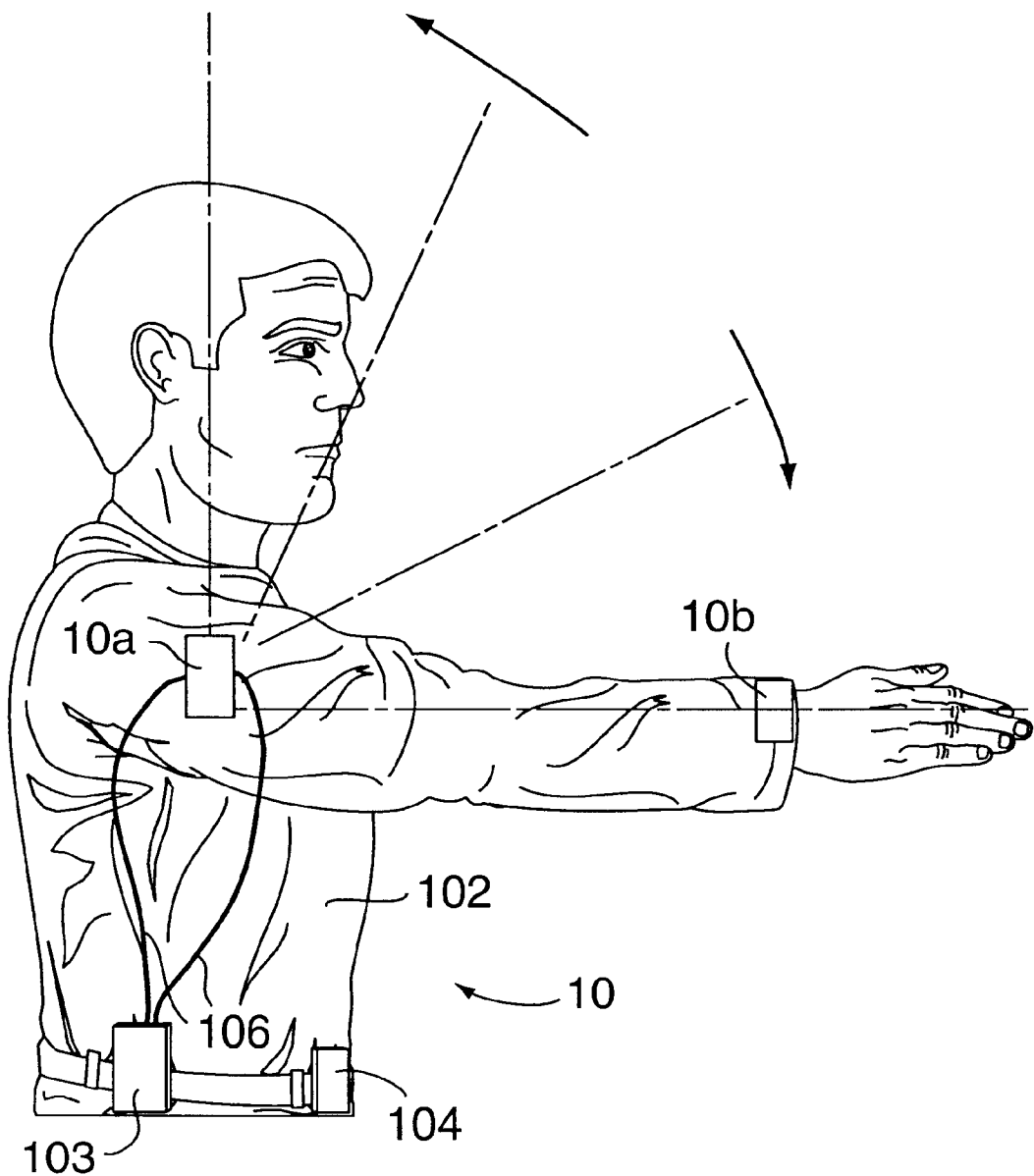
FIG. 1 schematically illustrates a portable sensor system in accordance with the present invention positioned on an object, such as a part of a person's body to determine the orientation of the object relative to a reference magnetic field.

Turning to FIG. 1, at least one portable sensor system 10 is positioned on an object such as portion of a human body. For example, as shown in FIG. 1, two sensor modules 10a, 10b are coupled to a person's shoulder and wrist, respectively, to keep track of the angular position of the body segments with respect to an ambient or reference magnetic field vector, such as the Earth's magnetic field vector. As few as one sensor module or as many as twelve such modules may be typically provided on a human body to determine orientations of various body segments. The sensor system 10 may also include a signal conditioning and data recorder or radio telemetry unit 102 shown strapped to the waist of the tested person. A battery pack 104 for powering the unit 102 and the sensor modules 10a, 10b may also be provided, and is shown also to be strapped to the waist. As shown in FIG. 1, electrical wires 106 may be employed for communication among the sensor modules 10a, 10b, the unit 102 and the battery pack 104.

Figure 2:
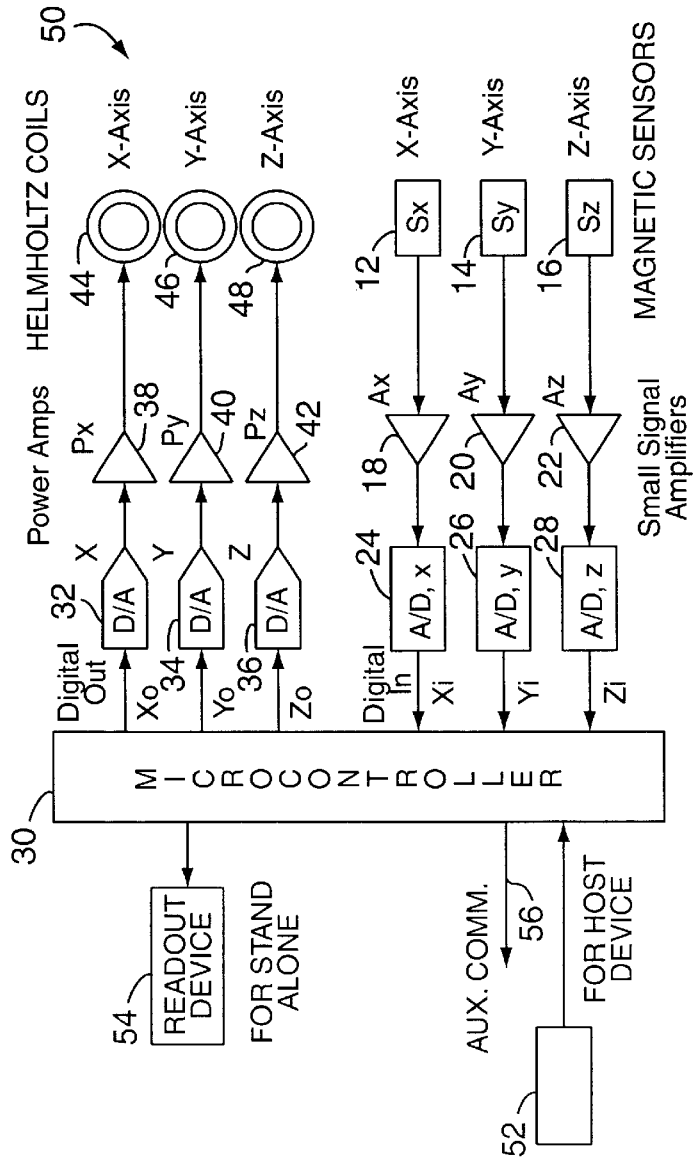
FIG. 2 an electrical circuit schematic of the sensor system of FIG. 1.

Turning now to FIG. 2, each sensor system module 10 includes first, second, and third magnetic sensors 12, 14, 16 that are fixed to, or located adjacent to and directed outwardly in fixed directions relative to a three-dimensional object, such as the human shoulder and wrist portions shown in FIG. 1, whose orientation is to be determined. The sensors may be any bipolar or unipolar magnetic sensors with sufficient sensitivity to measure a weak magnetic field such as the Earth's magnetic field, which averages approximately 0.5 gauss. Sensors suitable for use are readily available commercial devices such as fluxgate, Hall effect, and magnetoresistive sensors, and preferably are conventional magnetoresistive sensors, such as the KMZ10A model available from Philips Components. Each of the magnetic sensors 12, 14, 16 is directed in an orthogonal direction relative to the other two magnetic sensors so that each magnetic sensor detects one directional component of a magnetic field vector having as many as three directional components in three-dimensional space.

As shown in FIG. 2, the first, second and third magnetic sensors 12, 14, 16 are preferably coupled to input terminals of first, second and third small signal amplifiers/filters 18, 20, 22, respectively. The output terminals of the first, second and third small signal amplifiers 18, 20, 22 are respectively coupled to input terminals of first, second and third analog-to-digital (A/D) converters 24, 26, 28 via analog lines. Output terminals of the first, second and third A/D converters 24, 26, 28 are coupled to a conventional controller via digital lines. The controller 30 may be coupled to a host device, such as a computer 52, for receiving command signals to perform a magnetic angle scanning operation. The controller 30 may further communicate with a readout device 54, and other external devices (not shown) via auxiliary communication bus 56. The controller 30 is further coupled to input terminals of first, second and third digital-to-analog (D/A) converters 32, 34, 36 via digital output lines. Output terminals of the D/A converters 32, 34, 36 are respectively coupled to input terminals of first, second and third power amplifiers 38, 40, 42. Output terminals of the power amplifiers 38, 40, 42 are respectively coupled to first, second and third windings 44, 46, 48 of a three-axis Helmholtz coil system 50 that produces a modifiable magnetic field, the purpose of which will be explained hereinbelow.

A Helmholtz coil system by definition includes for each axis a pair of identical cylindrical coils of wire connected in series with one another. The coils are coaxial with one another and separated by a distance generally equal to the radius of the coils. When an electrical current passes through the coils, a uniform magnetic field is produced over a considerable volume on either side of the midpoint between the coils so as to generally mimic the form of a magnetic field generated by a long solenoid. The magnitude of the generated magnetic field is proportional to the applied current, the number of turns of the coils, and the size and spacing of the coils. The volume of the uniform magnetic field generated is primarily dependent on the size and spacing of the coils. Helmholtz coils are commonly employed to calibrate magnetic field sensors and navigational equipment, and to determine the effects of magnetic fields on the operation of various devices.

Figure 3:
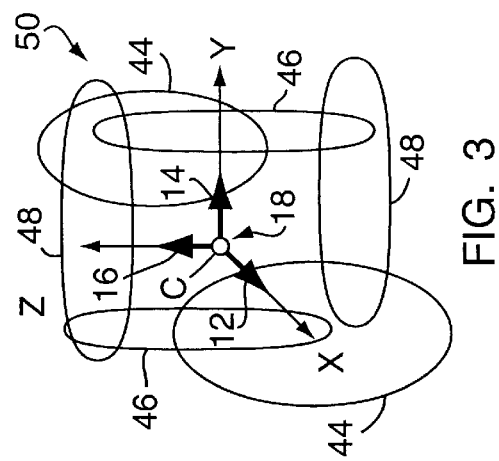
FIG. 3 schematically illustrates a three-axis Helmholtz coil system employed for generating a modifiable magnetic field in accordance with the present invention.

As schematically shown in FIG. 3, the three orthogonally directed, magnetic sensors 12, 14, 16 are centered within the three-axis Helmholtz coil system 50 and are directed outwardly from and in fixed relation to the object. The direction of orientation of each of the magnetic sensors 12, 14, 16 defines a separate axis of a coordinate system, such as the Cartesian coordinate system shown in FIG. 3. For example, as shown in FIG. 3, the first magnetic sensor 12 is directed in the x-coordinate direction, the second magnetic sensor 14 is directed in the y-coordinate direction and the third magnetic sensor 16 is directed in the z-coordinate direction. The magnetic sensors 12, 14, 16 thus are oriented with respect to the object to detect components of a magnetic field vector in the x, y, and z-coordinate directions, respectively.

Because the magnetic sensors 12, 14, 16 are directed outwardly in fixed relation to the object, the coordinate system defined by the direction of the magnetic sensors is in fixed orientation relative to the object, and therefore the coordinate system may reference the instantaneous orientation of the movable object relative to that of a reference magnetic field vector such as the Earth's magnetic field vector.

The Helmholtz coil system 50 is also to be in fixed orientation with respect to the object, and in turn, the coordinate system. For example, the first, second and third windings 44, 46, 48 of the three-axis Helmholtz coil system 50 respectively extend along the x-coordinate direction, the y-coordinate direction and the z-coordinate direction. Alternatively, each of the magnetic sensors 12, 14, 16 may be centered with a separate single-axis Helmholtz coil system, with each of these coils and magnetic sensors, in turn, oriented in one of the orthogonal x, y, z-coordinate directions.

As the orientation of the object changes with respect to the direction of a reference magnetic field, the coordinate system defined by the direction of the magnetic sensors 12, 14, 16 in turn changes in orientation with respect to the reference magnetic field to thereby reference or track the object's instantaneous orientation relative to the reference magnetic field.

In operation, the controller 30, which may receive a command signal from the computer 52, drives the D/A converters 32, 34, 36 to generate a modifiable magnetic field, preferably approximately equal in magnitude to that of the reference magnetic field, such as the Earth's magnetic field. The direction and magnitude of the electrical currents amplified by each of the power amplifiers 38, 40, 42 and driven through each of the first, second and third windings 44, 46, 48 of the Helmholtz coil system 50 determine the magnitude and direction of one of the three directional components of the modifiable magnetic field vector in three-dimensional space. The controller 30 repeatedly changes the direction and magnitude of the drive currents in each of the windings 44, 46, 48 according to a known, predetermined pattern to change the vector components of the modifiable magnetic field such that the orientation of the modifiable magnetic field is substantially moved in small angle increments throughout the coordinate system.

Figure 4:
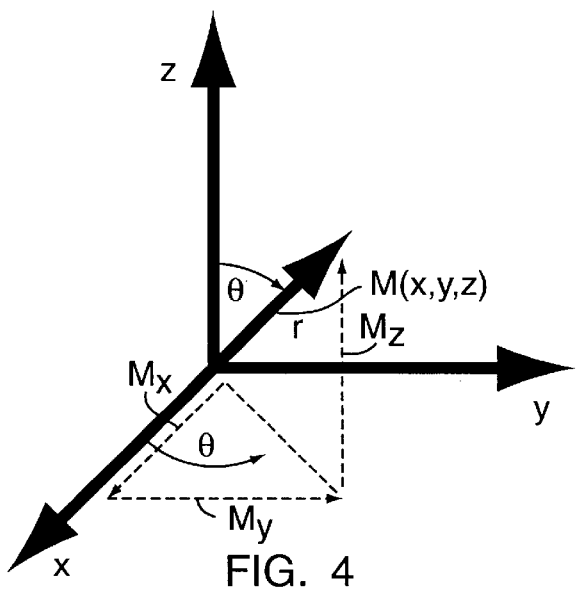
FIG. 4 is a vector diagram illustrating the predetermined pattern of changing the direction of the modifiable magnetic field in accordance with the present invention.

As shown in FIG. 4, for example, a modifiable magnetic field vector M(x,y,z), having a magnitude "r" equal to that of the reference magnetic field, includes three directional vector components Mx, My, and Mz. The magnitude r of the modifiable magnetic field vector M(x,y,z) is equal to the square root of the sum of the squares of the magnitudes of the three directional components Mx, My, Mz. The magnetic sensors 12, 14, 16 respectively detect the magnitudes of the vector components Mx, My, Mz of the modifiable magnetic field vector M(x,y,z). The modifiable magnetic field vector M(x,y,z) is changed in orientation in small angle increments by the controller 30 substantially through an entire directional coordinate system. For example, the modifiable magnetic field vector M(x,y,z) is incrementally changed in orientation in small angle increments relative to the z-axis from the angle q=0° (0 radians) to q=180° ($\pi$ radians). For each increment of the angle q, the angle f relative to the X-axis is changed in small angle increments from f=0° (0 radians) to f=360° ($2\pi$ radians). The controller 30 incrementally changes the orientation of the modifiable magnetic field vector by employing known coordinate-shifting algorithms to change the polarity and magnitude of the drive currents through each of the windings 44, 46, 48 of the Helmholtz coil system 50 according to a predetermined pattern or sequence. The changing drive currents in turn change the directional components Mx, My, Mz of the modifiable magnetic field so as to incrementally move or shift the orientation of the modifiable magnetic field vector M(x,y,z) substantially throughout an entire coordinate system. The small angle increments may, for example be 1° increments for compass applications or as little as 1/10° for guidance applications.

Figure 5A:
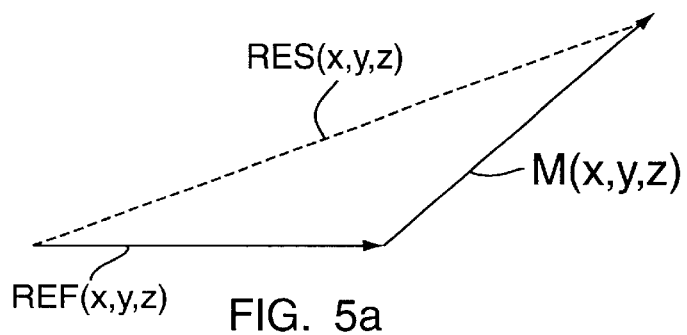
FIG. 5a is a vector diagram illustrating a first spatial relationship between a reference magnetic field vector and a modifiable magnetic field vector which are summed to form a resultant magnetic field vector.
Figure 5B:
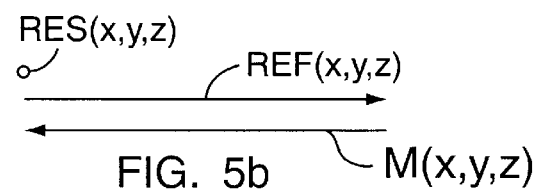
FIG. 5b is a vector diagram illustrating a second spatial relationship between a reference magnetic field vector and a modifiable magnetic field vector which are summed to form a resultant magnetic field vector.
Figure 5C:
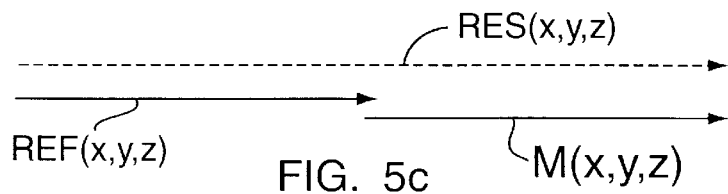
FIG. 5c is a vector diagram illustrating a third spatial relationship between a reference magnetic field vector and a modifiable magnetic field vector which are summed to form a resultant magnetic field vector.

The magnetic sensors 12, 14, 16 each sense a vector component of a resultant magnetic field which is the vector sum of the reference magnetic field vector and the modifiable magnetic field vector. FIGS. 5a–5c are vector diagrams which illustrate various spatial relationships between a reference magnetic field vector, REF(x,y,z), and a modifiable magnetic field vector, M(x,y,z) which are naturally summed to form a resultant magnetic field vector, RES(x,y,z). FIG. 5a shows that the resultant magnetic field vector is oriented in a different direction than either the reference or modifiable magnetic field vectors when the reference and modifiable magnetic field vectors are non-parallel. FIG. 5b shows that when the modifiable magnetic field vector is of approximately equal magnitude and oriented in the opposite direction relative to the reference magnetic field vector, the modifiable magnetic field cancels or otherwise minimizes the reference magnetic field (i.e., the magnitude of the resultant magnetic field vector is zero or minimized). FIG. 5c shows that when the modifiable magnetic field vector is of approximately equal magnitude and oriented in the same direction relative to the reference magnetic field vector, the modifiable magnetic field reinforces the reference magnetic field (i.e., the magnitude of the resultant magnetic field vector is twice that of the reference magnetic field vector or is otherwise maximized).

For each increment in which the controller 30 changes the orientation of the modifiable magnetic field vector M(x,y,z), the magnetic sensors 12, 14, 16 respectively detect the magnitude of its vector components Mx, My, Mz. The component signals of the modifiable magnetic field are amplified by the small signal amplifiers 18, 20, 22 and then converted to digital signals by the A/D converters 24, 26, 28. The controller 30 then calculates the square root of the sum of the squares of the magnitudes of the vector components Mx, My, Mz to determine the orientation of the modifiable magnetic field vector M(x,y,z). The controller 30 then determines the orientation of the modifiable magnetic field vector M(x,y,z) which cancels or otherwise minimizes the reference magnetic field (i.e., minimizes or zeroes the magnitude of the resultant magnetic field vector whose components are respectively detected by the magnetic sensors 12, 14, 16).

In other words, if one of the incrementally changed orientations of the modifiable magnetic field vector M(x,y,z) is approximately equal in magnitude and directed in an opposite direction relative to that of the reference magnetic field vector, such as the Earth's magnetic field vector, the magnitude of each component of the resultant magnetic field vector respectively detected by the magnetic sensors 12, 14, 16 will be zero or otherwise minimized. When this zero or null condition is found the controller 30 saves the x, y, z drive components of the electrical current through the Helmholtz coil system 50 used to generate the modifiable magnetic field vector whose known direction contributes to a null resultant magnetic field. Because the direction of the modifiable magnetic field vector at the moment of cancellation or minimization extends in the opposite direction to that of the reference magnetic field, the known direction of the modifiable magnetic field determines indirectly the orientation of the object relative to the reference magnetic field. Because the magnetic field sensors 12, 14, 16 are employed to determine the orientation of an object where the resultant magnetic field is nulled or otherwise minimized, the magnitude of the local reference or Earth's magnetic field does not need to be known to determine orientation.

Alternatively, another method for determining the orientation of the object in a reference magnetic field is to search by means of the controller 30 for the direction (i.e., determine the x,y,z vector components) of the known modifiable magnetic field vector which contributes to a resultant magnetic field vector having a magnitude which is maximized as detected by the magnetic sensors 12, 14, 16. The magnitude of the resultant magnetic field will be double that of the reference magnetic field if the magnitude of the modifiable magnetic field happens to be the same magnitude as that of the reference magnetic field. Because the magnetic field sensors 12, 14, 16 are employed to determine the orientation of an object where the resultant magnetic field is maximized, the magnitude of the local reference or Earth's magnetic field does not need to be known to determine orientation.

This maximization of the reference magnetic field vector occurs when the direction of the modifiable magnetic field vector is parallel with and in the same direction as that of the reference magnetic field vector. The x, y, z vector drive current components of the Helmholtz coil system 50 supplied by the controller 30 to generate the modifiable magnetic field vector are true x, y, and z vector components in magnitude and polarity. These known components of the modifiable magnetic field vector may then be converted to, for example, spherical coordinates, as shown in FIG. 4, to determine the orientation of the reference magnetic field vector, such as the Earth's magnetic field vector, relative to the object. The sensor system 10 may determine the orientation of the Earth's magnetic field vector in a full spherical coordinate system, which permits true three-dimensional measurement of angular displacement.

In the practical application of the sensor system 10, the time required to sample the vector space about the object may be greatly reduced by measuring the polarity of the magnetic sensors 12, 14, 16 relative to the reference or Earth's magnetic field as a first step before performing a full scanning operation by changing the direction of the modifiable magnetic field, as described above. The polarity of each of the magnetic sensors 12, 14, 16 will respectively indicate the specific quadrant to be searched in each of the xy plane, the xz plane and the yz plane, thereby effectively eliminating the requirement of searching all quadrants. Searching one or more quadrants with a coarse increment, and then searching a single quadrant in finer increments significantly reduces the response time of the sensor system 10.

Since most magnetic sensors can only sense sums of vector components, the sensor system 10 embodying the present invention simplifies the solution for finding the vector orientation of the Earth's magnetic field by zeroing out or otherwise minimizing the Earth's magnetic field from the standpoint of the magnetic sensors 12, 14, 16 according to one aspect of the invention described above. By zeroing out the Earth's magnetic field, the vector components are supplied by the drive windings 44, 46, 48 of the Helmholtz coil system 50, which in turn results in true x, y, and z components in polarity and magnitude. The magnetic sensors 12, 14, 16 within the three-axis Helmholtz coil system 50 are used only to show the presence of the resultant magnetic field which is the vector sum of the Earth's magnetic field and the modifiable magnetic field generated by the Helmholtz coil system 50. As such, the magnetic sensors 12, 14, 16 need not be drift-free or precisely calibrated. The sensor system 10 will read the coordinate direction of the Earth's magnetic field vector over a full spherical coordinate system which permits the sensor system to give compass (yaw), roll, and pitch information. Used as a compass, and compensated for the change in the inclination angle of the Earth magnetic field vector in geographic space, the sensor system 10 is a true solid-state, strapdown device requiring no gimbaling or mechanical roll/pitch sensors to compensate for off-axis operation. Integrated with a GPS system and data available from the World Magnetic Model, published by the U.S. Geological Survey National Geomagnetic Information Center, the sensor system 10 may be used as a compass anywhere on the face of the Earth.

The sensor system 10, as opposed to conventional magnetometers, does not require information regarding the local magnetic field vector. The sensor system 10 measures orientation relative to the reference magnetic field, regardless of its magnitude or direction. The magnetic sensors 12, 14, 16 within the three-axis Helmholtz coil system 50 are not used to directly measure the imposed magnitude of the Earth's magnetic field, but are employed merely to show the presence of the Earth's magnetic field or to determine where the magnitude of the resultant magnetic field is minimized or maximized. Thus the characteristics of the magnetic sensors 12, 14, 16 are less critical to system performance than with magnetometers. Since the sensor system 10 searches for a null condition, changes in the gain or sensitivity of the magnetic sensors 12, 14, 16 will not affect the accuracy of the measurements, as long as these changes do not occur during a measurement period. Also, minor offsets, sensor mismatch, and drift associated with temperature will not have a significant effect on the ability of the sensor system 10 to accurately determine orientation of an object with respect to the reference magnetic field vector.

Although offset changes in the magnetic sensors 12, 14, 16 cannot be distinguished from changes in orientation, a relatively simple procedure can be used with the sensor system 10 to compensate for changes in offsets. Before spatial orientation measurements are made, each of the magnetic sensors 12, 14, 16 should be placed in a reference orientation and allowed to self-calibrate. In contrast to conventional magnetometers, the sensor system 10 can re-calibrate without any intervention from the user, by driving the Helmholtz coil system 50 to conduct a complete spherical scan of the magnetic sensors. This self-calibration can be completed in a matter of seconds, and then becomes the reference orientation for the subsequent measurements made with this sensor. All signal changes after the self-calibration are assumed to be associated with changes in orientation. As long as the sensor offsets remain constant, the accuracy of subsequent measurements will be preserved.

As with any orientation sensor referenced to a magnetic field, the accuracy of these measurements is dependent on the uniformity of the reference magnetic field. If the measurements of interest are the relative orientations between multiple magnetic sensors, then the accuracy of these measurements will not be diminished if the reference magnetic field changes with time or position, as long as all the magnetic sensors are exposed to the same magnetic field at any given time. However, changes in the reference magnetic field must be slow with respect to the time needed to measure orientation, which is less than 20 ms when the magnetic sensors 12, 14, 16 are sampled at, for example, 50 Hz.

If the measurements of interest are the absolute orientations of the sensor system 10 relative to a local coordinate system, or reference orientation, then a fixed-position magnetic sensor can be used to establish the reference orientation. Even if the reference magnetic field changes over time, the accuracy of the orientation measurements will be preserved as long as the magnetic sensors, including the reference magnetic sensor, are exposed to the same magnetic field at any given time. In this configuration, the reference sensor provides a reference orientation, as well as information regarding changes in the reference magnetic field during the measurement period.

Although this invention has been shown and described with respect to an exemplary embodiment thereof, it should be understood by those skilled in the art that the foregoing and various other changes, omissions, and additions in the form and detail thereof may be made therein without departing from the spirit and scope of the invention. Accordingly, the present invention has been shown and described by way of illustration rather than limitation.

What is claimed is:

1. A method of determining the orientation of an object relative to a reference magnetic field, comprising the steps of:

establishing adjacent to the object a modifiable magnetic field;

changing the direction of the modifiable magnetic field among a plurality of predetermined, known orientations relative to the object;

repeatedly measuring adjacent to the object a resultant magnetic field, including the reference magnetic field and the changing modifiable magnetic field, the step of measuring being directed outwardly from adjacent to the object in predetermined directions that are fixed relative to the object; and determining when the magnitude of the resultant magnetic field is minimized or maximized indicating that the direction of the modifiable magnetic field is parallel with that of the reference magnetic field, and thereupon correlating the orientation of the object to the known orientation of the modifiable magnetic field.

2. A method as defined in claim 1, wherein the determining step includes determining when the magnitude of the resultant magnetic field is about zero.

3. A method as defined in claim 1, wherein the determining step includes determining when the magnitude of the resultant magnetic field is about twice that of the reference magnetic field.

4. A method as defined in claim 1, wherein the reference magnetic field is the Earth's magnetic field.

5. A method as defined in claim 1, wherein the step of changing the direction of the modifiable magnetic field includes:

changing in small angle increments the direction of the modifiable magnetic field, relative to a first coordinate axis, from an angle of about 0° to an angle of about 180°; and changing in small angle increments the direction of the modifiable magnetic field, relative to a second coordinate axis that is orthogonal to the first coordinate axis, from an angle of about 0° to about 360° for each increment of change in orientation about the first coordinate axis.

6. A method as defined in claim 5, wherein the steps of changing in small angle increments relative to the first and second coordinate axes are in angle increments from about $\frac{1}{10}$° to about 1°.

7. A method as defined in claim 1, wherein the step of establishing a modifiable magnetic field includes:

providing a Helmholtz coil system generally adjacent to the object, the Helmholtz coil system including windings extending in three coordinate axes, each of the axes being generally orthogonal relative to each other; and generating an electrical current through windings of at least one coordinate axis.

8. A method as defined in claim 7, wherein the step of changing the direction of the modifiable magnetic field includes incrementally changing the magnitude and polarity of currents through the windings of the Helmholtz coil system according to a predetermined sequence.

9. A method as defined in claim 1, wherein the step of measuring includes providing three magnetic sensors each to be oriented in a direction that is fixed relative to the object and in a direction which is orthogonal relative to that of the other two magnetic sensors.

10. A method as defined in claim 1, wherein the magnetic sensors are selected from the group consisting of fluxgate sensors, Hall effect sensors, and magnetoresistive sensors.

11. An apparatus for determining the orientation of an object relative to a reference magnetic field, the apparatus comprising:

first means for establishing generally adjacent to the object a modifiable magnetic field;

second means for changing the direction of the modifiable magnetic field among a plurality of predetermined, known orientations relative to the object;

third means for repeatedly measuring adjacent to the object a resultant magnetic field, including the reference magnetic field and the modifiable magnetic field, the measuring being directed outwardly from adjacent to the object in predetermined directions that are fixed relative to the object; and fourth means for determining when the magnitude of the resultant magnetic field is minimized or maximized indicating that the direction of the modifiable magnetic field is parallel with that of the reference magnetic field, and thereupon correlating the orientation of the object to the known orientation of the modifiable magnetic field.

12. An apparatus as defined in claim 11, wherein the first means for establishing the modifiable magnetic field includes a Helmholtz coil system having windings extending in three coordinate axes, each of the axes being generally orthogonal relative to each other.

13. An apparatus as defined in claim 11, wherein the second means for repeatedly changing the direction of the modifiable magnetic field includes a controller.

14. An apparatus as defined in claim 13, wherein the controller changes in small angle increments the direction of the modifiable magnetic field, relative to a first coordinate axis, from an angle of about 0° to an angle of about 180°, and further changes in small angle increments the direction of the modifiable magnetic field, relative to a second coordinate axis that is orthogonal to the first coordinate axis, from an angle of about 0° to about 360° for each increment of change in orientation about the first coordinate axis.

15. An apparatus as defined in claim 14, wherein the small angle increments are from about $\frac{1}{10}$° to about 1°.

16. An apparatus as defined in claim 11, wherein the third means for measuring a resultant magnetic field includes at least one magnetic sensor located adjacent to and in fixed orientation with respect to the object.

17. An apparatus as defined in claim 16, wherein the at least one magnetic sensor includes three magnetic sensors each directed in a direction that is orthogonal relative to that of the other two magnetic sensors.

18. An apparatus as defined in claim 16, wherein the at least one magnetic sensor is selected from the group consisting of fluxgate sensors, Hall effect sensors, and magnetoresistive sensors.

19. An apparatus for determining the orientation of an object relative to a reference magnetic field, the apparatus comprising:

a Helmholtz coil system having windings extending in three coordinate axes for generating a modifiable magnetic field when electrical current is passed through the windings, each of the axes being generally orthogonal relative to each other;

a controller for directing current to the Helmholtz coil system and repeatedly changing the polarity and magnitude of the electrical current through each of the windings among a plurality of predetermined, known orientations relative to the object, and for determining when a resultant magnetic field, including the reference magnetic field and the modifiable magnetic field, is minimized or maximized indicating that the reference magnetic field is parallel to the known orientation of the modifiable magnetic field; and at least one magnetic sensor communicating with the controller, the at least one magnetic sensor to be located adjacent to and in fixed orientation relative to the object for detecting the resultant magnetic field.

20. An apparatus as defined in claim 19, wherein the at least one magnetic sensor includes three magnetic sensors each to be oriented in a direction that is fixed relative to the object and in a direction which is orthogonal relative to that of the other two magnetic sensors.

21. An apparatus as defined in claim 19, further including at least one digital-to-analog converter and at least one power amplifier interposed between the controller and the Helmholtz coil system for converting digital signals from the controller into electrical current signals of predetermined polarity and magnitude.

22. An apparatus as defined in claim 19, further including at least one small signal amplifier and at least one analog-to-digital converter interposed between the at least one magnetic sensor and the controller for amplifying analog signals received from the at least one magnetic sensor and converting the signals into digital form for processing by the controller.

* * * * *